US009707028B2

(12) United States Patent
Batchelor et al.

(10) Patent No.: US 9,707,028 B2
(45) Date of Patent: Jul. 18, 2017

(54) MULTI-MODE COMBINATION ELECTROSURGICAL DEVICE

(71) Applicant: GYRUS ACMI, INC., Southborough, MA (US)

(72) Inventors: Kester J. Batchelor, Mound, MN (US); Theodore Blus, Shoreview, MN (US); Richard J. Curtis, Maple Grove, MN (US)

(73) Assignee: GYRUS ACMI, INC., Southborough, MA (US)

( * ) Notice: Subject to any disclaimer, the term of this patent is extended or adjusted under 35 U.S.C. 154(b) by 24 days.

(21) Appl. No.: 14/830,255

(22) Filed: Aug. 19, 2015

(65) Prior Publication Data

US 2016/0051314 A1    Feb. 25, 2016

Related U.S. Application Data

(60) Provisional application No. 62/039,506, filed on Aug. 20, 2014.

(51) Int. Cl.
*A61B 18/14*   (2006.01)
*A61B 17/28*   (2006.01)
(Continued)

(52) U.S. Cl.
CPC ...... *A61B 18/1442* (2013.01); *A61B 17/2812* (2013.01); *A61B 17/2833* (2013.01);
(Continued)

(58) Field of Classification Search
CPC ........ A61B 2018/1455; A61B 18/1442; A61B 17/29; A61B 2017/2946
See application file for complete search history.

(56) References Cited

U.S. PATENT DOCUMENTS

| 1,198,958 A | 9/1916 | Risely |
| 2,042,985 A | 6/1936 | Gardella |

(Continued)

FOREIGN PATENT DOCUMENTS

| CN | 1149519 A | 5/1997 |
| CN | 102164556 | 8/2011 |

(Continued)

OTHER PUBLICATIONS

International Search Report and Written Opinion for Application No. PCT/US2015/045850 dated Nov. 4, 2015.

(Continued)

*Primary Examiner* — Jocelyn D Ram
(74) *Attorney, Agent, or Firm* — The Dobrusin Law Firm, P.C.; Daniel P. Aleksynas

(57) ABSTRACT

An electrosurgical device comprising: (a) forceps including: a first working arm, and a second working arm; (b) a blade; (c) one or more sliders that move along the forceps between at least a first position and a second position; (d) a first activation button; and (e) a second activation button; wherein the electrosurgical device is capable of being switched between: (A) a first configuration wherein: the first working arm and the second working arm are free to move in a direction towards each other so as to grasp tissue therebetween, the blade is retracted within a distal end of the first working arm and a distal end of the second working arm, and the first activation button is configured to produce a first therapy signal; and (B) a second configuration wherein: the first working arm and the second working arm are secured together to prevent movement in a direction towards each other, and the blade is extended so that a distal end of the blade is substantially flush with the distal end of the first working arm and the distal end of the second working arm; wherein at least one of the one or more sliders (Continued)

disable the second activation button when the at least one slider is in a first position, and wherein the at least one slider in a second position: secures the first working arm and the second working arm so that movement of the first working arm and the second working arm are prevented in a direction towards each other, extends the blade, or enables the second activation button to produce a second therapy signal.

26 Claims, 5 Drawing Sheets

(51) Int. Cl.
    *A61B 17/295*      (2006.01)
    *A61B 18/08*      (2006.01)
    *A61B 18/00*      (2006.01)
    *A61B 17/00*      (2006.01)

(52) U.S. Cl.
    CPC .......... *A61B 17/295* (2013.01); *A61B 18/085* (2013.01); *A61B 18/1402* (2013.01); *A61B 2017/00411* (2013.01); *A61B 2018/00273* (2013.01); *A61B 2018/00607* (2013.01); *A61B 2018/1412* (2013.01); *A61B 2018/1455* (2013.01); *A61B 2018/1462* (2013.01)

(56) References Cited

U.S. PATENT DOCUMENTS

| | | |
|---|---|---|
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,443,935 A | 4/1984 | Zamba et al. |
| 4,463,759 A | 8/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dallemagne |
| 5,458,598 A | 10/1995 | Fienberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,658,281 A | 8/1997 | Heard |
| 5,693,052 A | 12/1997 | Weaver |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lindemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |

(56) References Cited

U.S. PATENT DOCUMENTS

| | | |
|---|---|---|
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,147,638 B2 | 12/2006 | Chapman et al. |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 * | 5/2016 | Shilev .......... A61B 18/042 |
| 9,358,065 B2 | 6/2016 | Ladtkow et al. |
| 9,439,665 B2 | 9/2016 | Marczyk et al. |
| 9,452,011 B2 * | 9/2016 | Batchelor .......... A61B 18/1233 |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0050633 A1 | 3/2003 | Ellman |
| 2003/0097126 A1 | 5/2003 | Woloszko |
| 2003/0109876 A1 | 6/2003 | Yamauchi |
| 2003/0114850 A1 | 6/2003 | McClurken et al. |
| 2003/0144652 A1 | 7/2003 | Baker et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 * | 5/2005 | Dumbauld .......... A61B 18/1445 606/45 |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 * | 4/2006 | Hushka .......... A61B 18/1445 606/42 |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van Wyk et al. |
| 2008/0147092 A1 | 6/2008 | Rogge et al. |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller et al. |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2013/0023874 A1 | 1/2013 | Lawes et al. |
| 2013/0066317 A1 | 3/2013 | Evans et al. |
| 2013/0079762 A1 | 3/2013 | Twomey et al. |
| 2013/0138096 A1 * | 5/2013 | Benn .......... A61B 18/1477 606/33 |
| 2013/0178852 A1 * | 7/2013 | Allen, IV .......... A61B 18/1442 606/42 |
| 2013/0237982 A1 * | 9/2013 | Rencher .......... A61B 18/1402 606/39 |
| 2013/0296846 A1 * | 11/2013 | Canady .......... A61B 18/042 606/37 |
| 2014/0100569 A1 | 4/2014 | Lawes et al. |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276795 A1 | 9/2014 | Batchelor et al. |
| 2014/0276796 A1 | 9/2014 | Batchelor et al. |
| 2014/0276797 A1 | 9/2014 | Batchelor et al. |

(56) References Cited

U.S. PATENT DOCUMENTS

| | | | |
|---|---|---|---|
| 2014/0276798 | A1 | 9/2014 | Batchelor et al. |
| 2014/0276799 | A1 | 9/2014 | Batchelor et al. |
| 2014/0276800 | A1 | 9/2014 | Batchelor et al. |
| 2014/0276804 | A1 | 9/2014 | Batchelor |
| 2015/0088138 | A1 | 3/2015 | Ranck et al. |
| 2015/0119885 | A1 | 4/2015 | Windgassen et al. |
| 2015/0148798 | A1 | 5/2015 | Windgassen et al. |
| 2015/0320485 | A1* | 11/2015 | Batchelor ............. A61B 18/08 606/41 |

FOREIGN PATENT DOCUMENTS

| | | |
|---|---|---|
| CN | 102836006 | 12/2012 |
| EP | 0392548 A | 10/1994 |
| EP | 1089664 | 4/2001 |
| EP | 1769765 A1 | 4/2007 |
| EP | 1530952 A1 | 7/2007 |
| EP | 1810629 A1 | 7/2007 |
| EP | 1977706 A1 | 10/2008 |
| EP | 2403422 | 1/2012 |
| JP | S50-143380 U | 11/1975 |
| JP | H10-137259 A | 5/1998 |
| JP | H10-504485 A | 5/1998 |
| JP | 2000070280 A | 3/2000 |
| JP | 2000210301 A | 8/2000 |
| JP | 2001029353 A | 2/2001 |
| JP | 2001170070 A | 6/2001 |
| JP | 2004508875 A | 3/2004 |
| JP | 2005144192 A | 6/2005 |
| JP | 2005521465 A | 7/2005 |
| JP | 2009247893 A | 10/2009 |
| JP | 2012518490 A | 8/2012 |
| WO | 96/05776 A1 | 2/1996 |
| WO | 99/66850 | 12/1999 |
| WO | 9966850 | 12/1999 |
| WO | 02/24089 A1 | 3/2002 |
| WO | 2006/122279 | 11/2006 |
| WO | 2007/002545 | 1/2007 |
| WO | 2007/093857 | 8/2007 |
| WO | 2010/101897 | 9/2010 |
| WO | 2012/053530 A | 4/2012 |
| WO | 2014/096815 A2 | 6/2014 |

OTHER PUBLICATIONS

315MHZ sliding remote cover, available at website : http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).
Potentially related U.S. Appl. No. 14/589,482, filed Jan. 5, 2015 published as 2015/0148798 on May 28, 2015.
Potentially related U.S. Appl. No. 14/589,515, filed Jan. 5, 2015, published as 2015/0119885 on Apr. 30, 2015.
Potentially related U.S. Appl. No. 14/829,725, filed Aug. 19, 2015.
Potentially related U.S. Appl. No. 14/830,069, filed Aug. 19, 2015.
Potentially related U.S. Appl. No. 14/177,780, filed Feb. 11, 2014, published as 2014/0276794 on Sep. 18, 2014.
Potentially related U.S. Appl. No. 14/178,411, filed Feb. 12, 2014, published as 2014/0276785 on Sep. 18, 2014.
Potentially related U.S. Appl. No. 14/178,569, filed Feb. 12, 2014, published as 2014/0276804 on Sep. 18, 2014.
Potentially related U.S. Appl. No. 14/178,577, filed Feb. 12, 2014, published as 2014/0276786 on Sep. 18, 2014.
Potentially related U.S. Appl. No. 14/205,598, filed Mar. 12, 2014, published as 2014/0276795 on Sep. 18, 2014.
Potentially related U.S. Appl. No. 14/205,919, filed Mar. 12, 2014 published as 2014/0276796 on Sep. 18, 2014.
Potentially related U.S. Appl. No. 14/209,071, filed Mar. 13, 2014 published as 2014/0276798 on Sep. 18, 2014.
Potentially related U.S. Appl. No. 14/210,535, filed Mar. 14, 2014, published as 2014/0276799 on Sep. 18, 2014.
Potentially related U.S. Appl. No. 14/210,741, filed Mar. 14, 2014, published as 2014/0276800 on Sep. 18, 2104.
Potentially related U.S. Appl. No. 14/211,042, filed Mar. 14, 2014, published as 2014/0276772 on Sep. 18, 2014.
Potentially related to U.S. Appl. No. 14/206,010, filed on Mar. 12, 2014, published as 2014/0276797 on Sep. 18, 2014.
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
Partial European Search Report for Application No. EP16206030 dated May 2, 2017.
Japanese Office Action for Application No. 2016-543610 dated May 18, 2017.

* cited by examiner

MULTI-MODE COMBINATION ELECTROSURGICAL DEVICE

FIELD

The present teachings generally relate to an electrosurgical device that can supply both monopolar power and bipolar power during a surgical procedure, and specifically to electrical forceps that can be mechanically reconfigured and then electronically reconfigured to switch between multiple modes during a surgical procedure.

BACKGROUND

Typically, electrosurgical devices have stand-alone monopolar capabilities or bipolar capabilities. Thus, a surgeon before a procedure begins may select either a device with monopolar capabilities or a device with bipolar capabilities and the surgeon can use the device to apply either monopolar power or bipolar power. For example, if the surgeon selects a monopolar device and monopolar power is not desired for a part of the surgical procedure the surgeon may use either the device that supplies monopolar power to perform that portion of the procedure or switch to a device with bipolar capabilities. Both of these devices may be used to perform the procedure, however, switching between devices and/or using a device that may be better suited for a different purpose may disturb the procedure flow, cause unnecessary delays in the procedure, and in some cases result in less than optimal energy sources being used.

Generally, electrosurgical devices are connected to a generator that produces a therapy signal and provides power to the electrosurgical device so that a therapy current is produced. However, the therapy currents that may be used are limited by the generator and thus if the generator is only capable of producing a single therapy current then only one therapy current can be applied through the electrosurgical device. Additionally, a generator may be capable of producing two therapy currents, but the electrosurgical device may only be capable of controlling and applying a single therapy current. Thus, the electrosurgical device may only apply a single therapy current. Some attempts have been made to produce a device that includes both monopolar capabilities and bipolar capabilities in a single device. These devices can be switched between monopolar capabilities and bipolar capabilities without switching devices. Some of these devices are reconfigurable between two mechanical configurations so that both monopolar and bipolar can be applied. However, the number of modes available in these devices may be restricted by the number of buttons available on the device.

Additionally, many surgical procedures require many different tools and each tool provides one or more functions that are useful during a surgical procedure. Thus, for each surgical procedure multiple different tools may be used by a surgeon to perform a surgical procedure. Changing between tools may lengthen a procedure or cause a surgeon to look away from a location and then require additional time or concentration to relocate a location of interest before continuing a procedure. Therefore, what is needed is a device that is capable of being mechanically reconfigured so that a surgeon can perform several steps with one instrument without having to change tools or field of view.

Examples of some electrosurgical instruments may be found in U.S. Pat. Nos. 6,110,171; 6,113,596; 6,190,386; 6,358,268; and 7,232,440; and U.S. Patent Application Publication Nos. 2005/0113827; 2005/0187512; 2006/0084973; 2012/0123405; 2014/0276795; and 2014/0276799 all of which are incorporated by reference herein for all purposes. It would be attractive to have an electrosurgical device that includes a single button that may be used to apply a monopolar therapy current and a bipolar therapy current. It would be attractive to have an electrosurgical device that may be mechanically reconfigured between three different mechanical configurations, which each apply a therapy current. What is needed is an electrosurgical device that produces more therapy currents than a generator supplies signals (i.e., generator modes) to the electrosurgical device and applies more modes than buttons available on the electrosurgical device. What is needed is a blade that is moved between three or more different configurations and in each different configuration one or more therapy currents are applied by the electrosurgical device that perform a different function.

SUMMARY

The present teachings meet one or more of the present needs by providing: an electrosurgical device comprising: (a) forceps including: a first working arm, and a second working arm; (b) a blade; (c) one or more sliders that move along the forceps between at least a first position and a second position; (d) a first activation button; and (e) a second activation button; wherein the electrosurgical device is capable of being switched between: (A) a first configuration wherein: the first working arm and the second working arm are free to move in a direction towards each other so as to grasp tissue therebetween, the blade is retracted within a distal end of the first working arm and a distal end of the second working arm, and the first activation button is configured to produce a first therapy signal; and (B) a second configuration wherein: the first working arm and the second working arm are secured together to prevent movement in a direction towards each other, and the blade is extended so that a distal end of the blade is substantially flush with the distal end of the first working arm and the distal end of the second working arm; wherein at least one of the one or more sliders disable the second activation button when the at least one slider is in a first position, and wherein the at least one slider in a second position: secures the first working arm and the second working arm so that movement of the first working arm and the second working arm are prevented in a direction towards each other, extends the blade, or enables the second activation button to produce a second therapy signal.

The present teachings provide an electrosurgical device comprising: forceps including: (1) a first working arm, (2) a second working arm, (3) a first activation button, (4) an optional second activation button, (5) one or more sliders, and (6) a toggle controller; wherein the electrosurgical device is capable of being switched between: a first configuration wherein: a toggle control button of the toggle controller is inactive or blocked, and the first therapy current passes between the first working arm and the second working arm; a second configuration wherein: the toggle control button is exposed when one of the one or more sliders are in the second position; and the toggle controller is configured to: toggle the first activation button to produce either the first therapy signal, a third therapy signal, or both; or toggle the optional second activation button to produce either a second therapy signal or a fourth therapy signal, or both.

The present teachings provide an electrosurgical device comprising: (a) forceps including: a first working arm, and a second working arm; (b) a blade electrode; wherein the electrosurgical device is capable of being switched between: (A) a first configuration wherein: the first working arm and second working arm are free to move in a direction towards each other so as to grasp tissue therebetween, the blade electrode is retracted within a distal end of the first working arm and a distal end of the second working arm, and the device is configured to produce a first electrosurgical therapy signal; and (B) a second configuration wherein: the first working arm and second working arm are secured together to prevent movement in a direction towards each other, and the blade electrode is extended so that a distal end of the blade electrode is substantially flush with the distal end of the first working arm and the distal end of the second working arm.

The present teachings provide: an electrosurgical device comprising: (a) a first slider that moves along the forceps between at least a first slider first position and a first slider second position; (b) a second slider that moves along the forceps between at least a second slider first position and a second slider second position; (c) a first activation button; and (d) a second activation button; wherein when the first slider is in the first slider first position: (i) the first working arm and second working arm are free to move in a direction towards each other so as to grasp tissue therebetween, (ii) the first activation button is configured to produce a first therapy signal, (iii) the second activation button is blocked or disabled, (iv) the second slider is prevented from moving from the second slider first position, and wherein when the first slider is in the first slider second position: (i) the second activation button is configured to produce a second therapy signal, and (ii) the second slider is permitted to move between the second slider first position and the second slider second position.

The teachings herein provide an electrosurgical device that includes a single button that may be used to apply a monopolar therapy current and a bipolar therapy current. The teachings herein provide an electrosurgical device that may be mechanically reconfigured between three different mechanical configurations, which each apply a therapy current. The teachings herein provide an electrosurgical device that produces more therapy currents than a generator supplies signals (i.e., generator modes) to the electrosurgical device and applies more modes than buttons available on the electrosurgical device. The teachings herein provide a blade that is moved between three or more different configurations and in each different configuration one or more therapy currents are applied by the electrosurgical device that perform a different function.

DETAILED DESCRIPTION

Figure 1:
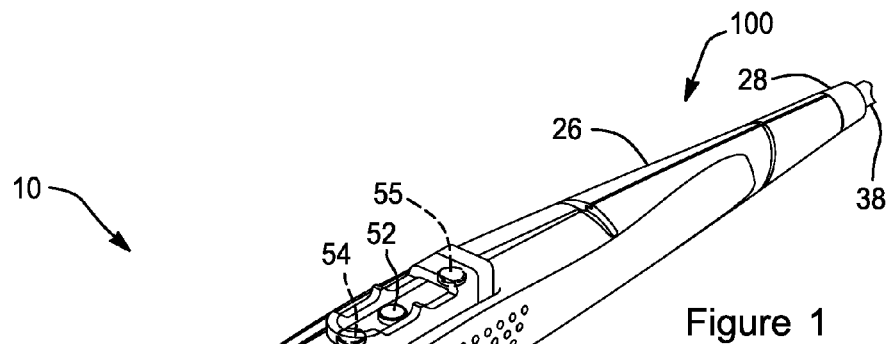
FIG. 1 is a perspective view of an electrosurgical device in a first configuration.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 62/039,506, filed on Aug. 20, 2014, the contents of which are incorporated by reference herein in their entirety for all reasons. The present teachings relate to an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. The electrosurgical system may include one or more handpieces as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may function to be switched between two or more configurations, two or more states, or both. For example, the electrosurgical device may be switched between a monopolar configuration, a bipolar configuration, a non-electrosurgical configuration, or a combination of the three. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both.

The electrosurgical device may be used to cut, perform hemostasis, coagulate, desiccate, fulgrate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an anatomical feature, an organ, a vein, skin, tissue, the like, or a combination thereof. In another example, one or more parts of the device may include a sharp edge and may be used to cut, similar to that of a scalpel. The electrosurgical device may include a handpiece and a generator. The electrosurgical device may have one or more therapy signals that extend between the handpiece and the generator.

The one or more therapy signals may be a signal, power, continuity, or a combination thereof. The therapy signals as discussed herein are electrosurgical therapy signals. The therapy signals may be a first electrosurgical therapy signal, a second electrosurgical therapy signal, a third electrosurgical therapy signal, a fourth electrosurgical therapy signal, or a combination thereof. The one or more therapy signals may extend from the handpiece to the generator or vice versa. The one or more therapy signals may be formed by the handpiece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be conducted when one or more of the sliders (e.g., a first slider or second slider) located on the handpiece are in a first position, a second position, a third position, or a combination thereof. The electrosurgical therapy signal may be a monopolar therapy signal, a bipolar therapy signal, or both. The electrosurgical therapy signal may be a monopolar cut, a monopolar coagulate, monopolar fulgate, a bipolar cut, a bipolar coagulate, a bipolar fulgate, or a combination thereof. The monopolar therapy signal may be any signal that has a voltage differential between a return port and an active port in the generator. The monopolar therapy signal is any signal that when applied by the electrosurgical device extends from one pole of an electrosurgical device to another pole located at a remote location, off of the electrosurgical device, off the handpiece, or a combination thereof. The monopolar therapy signal (i.e., current, voltage, power, or a combination thereof) extends from an electrode of the handpiece to an electrode that is not part of the handpiece or directly electrically connected to the handpiece. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a blade electrode to one or both working arms, or both). The therapy signal may be generated and conducted from the handpiece to the generator.

The generator may function to supply power, a therapy current, control signals, an electrosurgical therapy signal, or a combination thereof. The generator may function to be electrically connected to a handpiece to provide and/or receive electrosurgical therapy signals, power, therapy current, or a combination thereof. The generator may be capable of producing only a single therapy current. The generator may be capable of producing two therapy currents. The generator may include two or more power connections, three or more power connections, or four or more power connections. The power connections may be any port in the generator so that one or more power connectors of the handpiece may be plugged into so that power, control signals, therapy currents, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may include a central processing unit (CPU), a series of internal switching, or both. The CPU may be interchanged with the internal switching and the switching may perform the same functions as the CPU. The CPU or internal switching may be used to switch the electrosurgical device between a first configuration, a second configuration, a third configuration, a monopolar configuration, a bipolar configuration, a non-electrosurgical configuration, or a combination thereof. Preferably, the electrosurgical device is mechanically reconfigured between a first configuration and a second configuration and optionally to a third configuration.

The first configuration, second configuration, and third configuration are mechanical reconfigurations. The first configuration, second configuration, and third configuration may mechanically reconfigure the electrosurgical device so that the electrosurgical device provides different modes. For example, in a first configuration the electrosurgical device may only provide a bipolar therapy current. In the first configuration the blade may be in a retracted state. The first configuration may permit the working arms to be used as forceps, the working arms may move relative to each other, the working arms may laterally move (i.e., towards and away from each other such as in a gripping type direction), the working arms may not be inhibited by the blade, or a combination thereof. In the first configuration the other buttons (e.g., activation buttons or toggle control buttons) may be physically prevented from being actuated by structures of the handpiece (e.g., sliders). In another example, in a second configuration the electrosurgical device may include a monopolar cut, a monopolar coagulation, a bipolar cut, a bipolar coagulation, or a combination thereof. The first configuration, second configuration, and third configuration may be any of the various configurations discussed herein. The first configuration may provide a first therapy current. The first therapy current may be monopolar energy and/or monopolar current. Preferably, the first therapy current is bipolar energy and/or bipolar current. Bipolar energy is any power source that during application extends from one pole of an electrosurgical device to another pole on the same electrosurgical device. Stated another way, bipolar energy is energy that extends from one component of the handpiece to another component of the handpiece. For example, energy that extends between two working arms on the handpiece is bipolar energy, or energy that extends from a blade electrode to one or both working arms is a bipolar energy. The first electrical configuration may be deactivated by electrically disconnecting the one or more first activation buttons, covering the one or more first activation buttons, electrically disconnecting the blade electrode, electrically disconnecting one or both of the working arms, or a combination thereof.

The second configuration may provide a second therapy current or a second therapy signal (as discussed herein for all modes and configurations therapy current and therapy signal are used interchangeably). The second configuration may be a second mechanical configuration of the electrosurgical device. The second configuration may have the blade partially advanced relative to the working arms. Preferably, the second configuration, mechanically reconfigures the electrosurgical device (relative to the first configuration and the third configuration) so that the distal ends of the blade, first working arm, and second working arm are substantially flush (e.g., linear or in line) or slightly proud. The distal ends as discussed here are an end of a respective component that is farthest from the power cords and the part that points towards a user. Thus, the distal ends of the blade and working arms point away from a user during use. The distal ends may be substantially flush and may be located within about 3 mm or less, preferably about 2 mm or less, more preferably about 1 mm or less, or even about 0 mm of a central line (i.e., a line that extends perpendicular to a length of the blade and each of the three distal ends are substantially flush with that line (e.g., each distal end extends toward the line and within about 3 mm or less of that line)). More preferably, the distal ends of the blade, the first working arm, and the second working arm are flush and form a substantially straight line. The distal ends of the blade, the first working arm, the second working arm, or a combination thereof may provide one or more therapy currents and preferably a first therapy current and a second therapy current at different times, but without reconfiguring the electrosurgical device.

The second therapy current may be bipolar energy (e.g., bipolar current or bipolar power). Preferably, the second therapy current may be monopolar energy (e.g., monopolar current or monopolar power). Monopolar energy may be any power source that during application extends from one pole of an electrosurgical device to another pole located at a remote location, off of the electrosurgical device, off the handpiece, or a combination thereof. Stated another way, bipolar energy is energy that extends from one component of the handpiece to a component that is not part of the handpiece. For example, energy that extends from a blade electrode to a ground pad is monopolar energy, or energy that extends from one or both working arms to a ground pad is monopolar energy. More preferably, the second configuration provides a plurality of therapy currents and the device may be switched between therapy currents by changing the modes of the electrosurgical device. The second configuration may provide at least four different therapy currents. The at least four different therapy currents may include monopolar cut, monopolar coagulation, bipolar cut, and bipolar coagulation. The second electrical configuration may be deactivated by electrically disconnecting the one or more second activation buttons, covering the one or more second activation buttons, electrically disconnecting one or both working arms, electrically disconnecting the blade electrode, shorting the first working arm with the second working arm, or a combination thereof. The second configuration may switch between at least two of the different therapy currents by pressing a different activation button. In the second configuration the therapy currents available from each of the activation buttons may be changed by pressing the toggle control button and changing the mode of the electrosurgical device. The second configuration may create a coagulation therapy current by depressing a coagulation activation button and then almost instantly provide a cut therapy current by releasing the coagulation activation button and depressing a cut activation button. The second configuration may be converted into a third configuration or the second configuration may be bypassed so that the electrosurgical device is converted directly from a first configuration to a third configuration.

The third configuration may function to fully extend the blade and provide a plurality of therapy currents. Preferably, the third configuration provides at least one first therapy current and at least one second therapy current. More preferably, the third configuration provides at least four therapy currents (e.g., monopolar cut, monopolar coagulation, bipolar cut, bipolar coagulation). The third configuration may function to provide mechanical cutting. For example, the blade may be used as a mechanical cutting blade. The blade may be used as both a mechanical cutting blade and an electrical blade. The third configuration may provide any of the therapy currents taught herein for the second configuration. The blade may be extended beyond the distal ends of the first working arm and the second working arm so that the blade may contact a feature of interest and the working arms may not contact any features of interest. The third configuration may permit the second slider to move between two or more positions. The third configuration may be a monopolar configuration The device when in a monopolar configuration may supply power through a handpiece component (e.g., a blade electrode) and a return electrode that may be located at another location outside of the hand held portion of the electrosurgical device, through a handpiece component and an adjacent handpiece component, or both. The monopolar configuration may be any configuration where the electrosurgical device may be used to apply monopolar power. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. A monopolar configuration may be used so that power during use extends from a blade electrode to one or both bipolar electrodes, one or more working arms, one or more ground pads, or a combination thereof. Preferably, in a monopolar configuration a therapy current extends from a blade to a remote electrode. The remote electrode may be any electrode that is located remotely from the handpiece. The remote electrode may not be directly connected to the handpiece. For example, the remote electrode and handpiece may be connected through the generator. The remote electrode may be a ground pad. The remote electrode may be electrically connected to one or more of the electrodes on the handpiece through tissue or an anatomical feature of interest. The blade electrode when in the monopolar configuration may be used for less delicate procedures, less localized electrosurgery, or both when compared to bipolar electrosurgery.

The device when in a bipolar configuration may supply power from one portion of the device to a second portion of the device so that the return path for the power is relatively short when compared to the monopolar configuration. The bipolar configuration may be any configuration where the electrosurgical device may be used to apply bipolar power. The device when in the bipolar configuration may supply power between two localized handpiece components such as two working arms. The bipolar configuration may be used to coagulate, for hemostasis, cutting, fulguration, or a combination thereof. When in the bipolar configuration the electrosurgical device may include two opposing working arms. The two opposing working arms may be configured as forceps.

The forceps may function to grip, hold, squeeze, or a combination thereof one or more objects. The forceps may include one or more finger grips (i.e., configured like scissors) that may be used to move the forceps so that they may be used to grip one or more objects. The forceps may be free of finger grips and be actuated by direct pressure being applied to opposing sides of the forceps so that the forceps close and grip an object. The forceps may be tweezers or a tweezer like device. The forceps include at least two working arms, and preferably two opposing working arms.

The working arms (or jaws, but discussed herein as arms) may function to grip, hold, squeeze, or a combination thereof an object when the object is between the two or more opposing working arms. The working arms may include one or more gripping features that may assist in gripping, holding, squeezing, or a combination thereof an object. The working arms may be connected together by a central section. The central section may be a main body section of the electrosurgical device (or handpiece) that moves or permits movement of the working arms relative to each other. The working arms may be movable between two or more positions. Preferably, the working arms are movable between at least a first position and a second position. For example, the working arms may be movable between an open position (e.g., forceps) and a closed position (e.g., probe). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. More preferably, in the second position, the third position, or both the working arms are immobilized so that the working arms cannot be used a forceps. The working arms may be longitudinally static (i.e., static along the length of the arms) and laterally moveable (i.e., towards another working arm in a gripping motion) relative to each other. The working arms may be longitudinally moveable and may be moveable relative to each other so that a gripping force may be created. For example, the working arms when in a bipolar configuration may both be extended and then retracted so that a blade electrode may be exposed forming a monopolar configuration. In the immobilized state the first working arm and the second working arm may be laterally static and longitudinally static. Laterally static as discussed herein is that the working arms cannot move towards or away from each other or rotate about the longitudinal axis of the working arms. Preferably, in the second position and the third position the working arms are completely immobilized and cannot move in any direction relative to each other (i.e., lateral movement). The working arms may be retractable and/or extendable individually, simultaneously, or both. The working arms may be selectively retractable and/or extendable so that one or more tip regions are exposed relative to another working arm, the blade, or both.

The working arms include a tip region. The tip region may include a portion that is configured to assist in facilitating gripping, holding, squeezing, or a combination thereof. Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. The tip region of each of the working arms includes an electrode. Preferably, the first working arm includes a first electrode and the second working arm includes a second electrode. Each of the electrodes of each of the working arms are a point where power flows to or from each of the working arms. Preferably, the tip region includes insulation on the non-contact portions of the working arms so that electrosurgical energy is not transferred through incidental contact. The tip portion may include insulation on the tip regions. The insulation may cover any portion of the working arms except for the electrodes (e.g., first electrode or second electrode) so that power may pass to or from the electrodes. The working arms may include an active portion and an inactive portion (i.e., an insulated portion). The working arms may be immobilized by one or more mechanical features. Preferably, the mechanical features are one or more immobilization arms that extend from each of the one or more working arms or housing to restrain the working arms.

The one or more immobilization arms, one or more immobilization features, or both may be any feature of the housing, the working arms, or both that may immobilize one or both working arms when the electrosurgical device is in the second configuration, the third configuration, or both. The immobilization arms may be connected to the housing and extend between one or both of the working arms, and when the blade is advanced the immobilization arms are separated and the working arms are moved into contact with each other. The immobilization arms may be connected to the housing and extend between one or both of the working arms and when the blade is advanced, the immobilization arms are compressed, pushed together, or both and the working arms are moved into contact with the blade and immobolized. The immobilization arms may be generally parallel to the working arms, may extend: in the same direction as the working arms, may extend away from the working arms, towards an opposing working arm, towards the user, away from a user, or a combination thereof. The housing, the working arms, or both may be free of immobilization arms. An immobilization feature such as a wedge may be moved between the first immobilization arm and the second immobilization arm the immobilization arms may be moved into contact or spread apart so that the working arms are immobilized.

The two or more working arms may be immobilized by an immobilization feature. The immobilization feature may be any feature that connects or locks the two or more working arms together so that the arms are immobilized in the probe configuration, so that the forceps are disabled, or both. The immobilization features may be part of the arms, part of the housing, all or a part of the first slider, part of the second slider, or a combination thereof. The immobilization feature while being moved and immobilizing may move a blade, may extend a blade out a channel, from between the working arms, or a combination of both.

The blade may be any device that may be used to apply monopolar power during a procedure, that may be longitudinally movable, rotationally movable, extendable, retractable, to mechanically cut, or a combination thereof. The blade may function to apply a bipolar therapy current. The blade includes a blade electrode and the blade electrode applies or receives a therapy signal. The blade may be static. The blade electrode may be located within a distal end of a blade. The blade electrode may be part of the blade. The blade electrode may be a point, edge, or surface on the blade where power extends from, extends to, or both. Preferably, in one embodiment the blade may be static and the working arms are moved relative to the blade so that when the working arms are moved the blade is exposed. More preferably, the blade is movable. The blade may have a first position (e.g., retracted), a second position (e.g., partially extended), and a third position (e.g., fully extended). The first position may be where the blade is located relative to the working arms so that the working arms are past the distal end of the blade (e.g., the blade is retracted so that the working arms extend past the blade or the working arms are extended so that the working arms extend past the distal end of the blade). The second position may be where the distal end of the blade and the distal ends of the first working arm and the second working arm are substantially flush (e.g., within about 3 mm or less, preferably within about 2 mm or less, and more preferably within about 1 mm or less (i.e., about 0.75 mm)). Most preferably, flush means that the distal ends form a flat surface without one surface being forward or behind the other surfaces. The second position may immobilize the distal end of the blade and the distal ends of the working arms in a substantially flush configuration so that the distal end of the electrosurgical device is substantially flat. The third position may be where the distal end of the blade (i.e., the blade electrode) is located relative to the working arms so that the distal end of the blade is extended beyond the distal end of the working arms (e.g, the blade is extended so that the working arms are located proximate to the user or the working arms are retracted so that the blade is beyond the working arms). The blade and the working arms may be separated by an insulator or insulation in the first position, second position, third position, or a combination thereof. Preferably, insulation or an insulator is located between the blade and the working arms in at least the second position and the third position.

The insulator may function to prevent power and/or stray power from extending to and/or from the blade from the working arms. The insulation or insulator (hereinafter insulator) may prevent the blade, working arms, or both from creating a short, passing current to an undesired location, passing current from a location other than an electrode, or a combination thereof. The insulator may extend along all or a portion of the blade. The insulator may substantially surround all of the blade when the blade is in a retracted position, a bipolar configuration, a forceps configuration, probe configuration, or a combination thereof. The insulator may insulate the blade and blade electrode from stray current from the working arms, the ground pad, or both. The insulator may be a static component and the blade may move relative to the insulator. The insulator may move with the blade, the working arms, or both. The insulator may be made of insulative material so that the flow of current to and/or from the blade electrode is substantially prevented. The insulator may be made of and/or include rubber, plastic, silicone, an elastomer, silicone, PTFE, or a combination thereof. The insulator may be an insulator sleeve. The insulator sleeve may prevent power from passing to and/or from the blade electrode. Preferably, the insulator sleeve prevents power from passing to and/or from the blade when the blade is retracted so that the blade electrode is not powered, a circuit cannot be completed, or both. The insulator sleeve may be a sleeve that covers a portion of the blade. The insulator sleeve may move with the blade so that the same portions of the blade are always covered and the same portions of the blade electrode are always exposed. The insulator sleeve may be an integral part of the blade. The insulator sleeve may be fixedly connected to the blade, the working arms, or both. The insulator sleeve may move with the blade when the one or more sliders are moved.

The one or more sliders may function to cover one or more activation buttons, move one or more activation arms, move the blade, move one or both working arms, immobilize and/or electrically disconnect one or more features of the electrosurgical device, immobilize one or more activation buttons, impede movement and/or depression of one or more activation buttons, move one or more immobilization arms, toggle between one or more modes, prevent movement of one or more toggle control buttons, or a combination thereof. The one or more sliders may be a shield that covers the activation buttons that are not in use so that one or more of the activation buttons are protected from contact. For example, when the electrosurgical device is configured for bipolar use the slider may cover the monopolar activation buttons and expose the bipolar activation buttons or vice versa. The one or more sliders may be a component that is movable on the electrosurgical device and the sliders reconfigure all or a portion of the electrosurgical device when they are moved. The one or more sliders may be longitudinally movable along the electrosurgical device. The one or more sliders may lock the working arms, advance and retract the blade, or both. The sliders may be a solid piece. The electrosurgical device may include a plurality of sliders. Preferably, the electrosurgical device includes at least two sliders (i.e., a first slider and a second slider). The first slider may have a first slider first position, a first slider second position, first slider third position, or a combination thereof. The first slider first position may be a retracted position or a proximal position. The first slider second position may be an intermediate position (between a proximal position and a distal position) or a distal position. The first slider third position may be a distal position. The second slider may have a second slider first position, second slider second position, a second slider third position, or a combination thereof. The second slider first position may be a retracted position or a proximal position. The second slider second position may be an intermediate position (between a proximal position and a distal position) or a distal position. The second slider third position may be a distal position. The slider may have a domed structure that receives, extends over, prevents movement of, or a combination thereof one or more activation buttons, one or more toggle control buttons, or both. The slider may include one or more positions. Preferably, the sliders include at least a first position and a second position (e.g., a first electrical configuration, a second electrical configuration, forceps configuration, probe configuration). The sliders may have a plurality of positions (for example, the slider may be used to convert the electrosurgical device between three different configurations and thus, the slider may have three positions). Multiple sliders may be used to convert the electrosurgical device between the multiple configurations. For example, a first slider may mechanically convert the electrosurgical device from a first configuration to a second configuration and the second slider may mechanically convert the electrosurgical device from the second configuration to the third configuration. The slider in the first position, the second position, third position, or a combination thereof may perform any of the functions discussed herein for the slider. The sliders may each have a plurality of positions. The slider may be moved by sliding on a track. The sliders may move relative to the handpiece, the working arms, or both. The sliders may move in a linear manner relative to the working arms, handpiece, or both. The sliders may rotate relative to the handpiece, the working arms, or both. The slider may be part of a slider assembly that moves the blade. The first slider, second slider, or both may move the blade, immobilize the working arms, or both.

The first slider may prevent movement of the second slider or vice versa. For example, when in a first position the first slider may lock the second slider in an off position so that the toggle control button is covered. The first slider in a first position may prevent movement of the blade, moving the second slider so that the second slider changes modes, or both by locking the second slider in a first position.

One or more of the one or more sliders may be connected to one or more other devices that may be retracted. For example, one slider may be connected to the blade and the slider may be used to move the blade into and/or between a first configuration, second configuration, a third configuration, any other configuration, or a combination thereof. In another example, the slider may be connected to the working arms so that when the slider is moved the working arms are extended and/or retracted or laterally moved towards or away from each other. The slider may be integrally connected to the blade. The slider may include one or more electrical connectors. The one or more electrical connectors may function to pass power from a wire to an electrosurgical component or to change the modes of the electrosurgical device. For example, a wire may connect to an electrical connector and the electrical connector may power the blade electrode within the blade. The one or more electrical connectors may move with the slider so that as the slider is extended or retracted the electrosurgical device is electrically reconfigured through the mechanical movement. In another example, movement of the slider in a forward direction (e.g., a longitudinal direction) may electrically connect the ground pad to a power source and retraction of the slider may electrically disconnect the ground pad from the power source. The slider may have 2, 3, or even 4 electrical connectors. The slider may include an electrical connector for the first working arm, the second working arm, the ground pad, and the blade electrode. The slider may lock a device in a position, immobilize one or more working arms, or both. For example, the slider may lock the blade in a retracted position when the electrosurgical device is in a first configuration. In another example, the slider may lock the blade in a forward position and immobilize both of the working arms when the electrosurgical device is in a second configuration or a third configuration. The slider may lock by a detent, a projection that locks in a corresponding recess, a mechanical interlock, a friction fit, a mechanical lock, an electromagnetic latching system, or a combination thereof. This slider may be connected to one or both working arms of the electrosurgical device. The slider may be connected to a central section of the electrosurgical device. The one or more sliders in the first position, second position, third position, or a combination thereof may remain in contact with the central section. The one or more sliders by moving between the first position and second position and third position may change one or more switches in an activation circuit so that one or more modes of the electrosurgical device are changed.

The activation circuit may be any part of the electrical surgical system, handpiece, or both that may be activated so that one or more therapy currents are generated, applied, supplied, prevented from being supplied, or a combination thereof. The activation circuit may electrically connect two or more components, electrically activate two or more components, provide a user interface, or a combination thereof. The activation circuit may have one or more switch states, two or more switch states, or three or more switch states. The switch states may be changed as the one or more sliders are moved from a first position, a second position, a third position, or a combination thereof or the toggle controller is actuated (i.e., one or more toggle control buttons of the toggle controller), or both. The activation circuit and switch states may vary the path of a therapy signal from a generator so that the different modes are created upon activating one or more of the activation buttons.

The one or more activation buttons may function to control one or more functions of the electrosurgical device. The one or more activation buttons may control the bipolar power, the monopolar power, a bipolar cut setting, bipolar coagulation setting, a therapy current, a therapy signal, rotation of the blade, rotation of the monopolar electrode, a toggle controller, or a combination thereof. The one or more buttons may be exposed and/or unlocked by the slider as the slider moves, the blade moves, or both to and/or from a first configuration to a second configuration and a third configuration or vice versa. For example, the monopolar activation button may only be exposed when the slider, blade, or both are in the monopolar configuration. The monopolar activation button, the bipolar activation button, or both may turn on power to the respective electrode so that power is supplied to the area of interest. Each activation button may apply one therapy signal or therapy current at a time, however, each activation button may apply multiple modes by the electrosurgical device being changed between modes. For example, the first activation button may provide a first therapy signal when the toggle controller is in a first position and when the toggle controller is in a second position the same first activation button may provide a second therapy signal that is different from the first therapy signal. In another example, if there are two activation buttons located on an electrosurgical device then when the toggle controller is in a first position both activation buttons may provide a first therapy signal (e.g., a bipolar cut and bipolar coagulation) and when the toggle controller is moved to a second position both activation buttons may both provide a second therapy signal (e.g., monopolar cut and monopolar coagulation) and both of the first therapy signals are different from each other and both of the second therapy signals are different from each other. For example, the toggle controller may include one or more toggle control buttons and the toggle control buttons may be actuated so that the electrosurgical device is moved between modes. The toggle controller may change the therapy signals provided from the working arms, through the working arms, between the working arms, from the blade, to the blade, or a combination thereof when each of the activation buttons are activated.

The toggle controller may include one or more toggle control buttons. The toggle controller may include a plurality of toggle control buttons. The toggle controller may switch the electrosurgical device two or more modes. Preferably, a single toggle control button may toggle between a plurality of different modes. The toggle controller may function to change the electrosurgical device between two or more modes. The one or more toggle control buttons may toggle between two or more modes in each of the configurations of the electrosurgical device. The one or more toggle control buttons may toggle, or progress, between a plurality of modes. The toggle controller, the toggle control buttons, or both by toggling, may switch between modes or move a switch that changes modes. The toggle controller may toggle the electrosurgical device so that when the activation buttons are depressed the therapy signal provided from the electrosurgical device is changed from one mode to a different mode. The one or more toggle control buttons may electrically change the electrosurgical device between modes, may mechanically change the electrosurgical device between modes, or both. The toggle controller, the toggle control buttons, or both may be locked in a single mode when the electrosurgical device is certain configurations (e.g., a first configuration or a bipolar configuration). The toggle control buttons may be a slider or part of a slider. The toggle control buttons may be free of physical movement along the handpiece, during actuation. The toggle control buttons may switch a mode in a generator, within the handpiece, or both. The toggle controller may be connected to a blade, a blade electrode, or both and may assist in moving the blade from a first position to a second position so that the mode of the electrosurgical device is changed from a first mode to a second mode.

The blade may function to electrically cut, mechanically cut, or both. The blade may be any part of the electrosurgical device that supplies power from one location to a distal location. The blade may be a combination of two or more devices that when combined may form a blade. The blade may be rotatable about its axis, longitudinally movable about the longitudinal axis, the longitudinal axis of the electrosurgical device, the working arms, or a combination thereof, be static, or a combination thereof. The blade may be blunt, have one or more sharpened edges, have dull edges, or a combination thereof. The blade may rotate to any angle about its longitudinal axis, so that the blade may be used to cut, be ergonomically oriented so that a user is not required to reposition their grip, used for vertical cutting, used for side to side cutting, or a combination thereof.

The handpiece may be any part of the device that the user grips, that houses one or more of the control buttons, toggle controller, one or more switches, one or more electrical connectors, one or more diodes, one or more capacitors, or a combination thereof. The handpiece may house all or a portion of the control circuitry, a central processing unit, or both. The handpiece may electrically connect the electrosurgical device, the electrical system, or both to the generator. The handpiece may both physically connect the functional elements of the electrosurgical device and electrically connect the elements of the electrosurgical device. The handpiece may be a body portion of the electrosurgical device, a portion between the two or more working arms, a connector between the two or more working arms, that houses all or a portion of the circuitry that includes an activation circuit, which includes one or more activation buttons, the toggle controller, the toggle control buttons, or a combination thereof. Preferably, the handpiece is the portion that a surgeon grips and presses one or more activation buttons to apply power to a desired location, change modes, or both. More preferably, the handpiece is a central section that includes two activation buttons, one toggle controller, and one or more electrical connectors for supplying power to the electrosurgical device, the working arms, the blade electrode, or a combination thereof. Most preferably, the handpiece includes two activation buttons, a toggle controller, and one or more sliders that that advance a blade and lock the working arms together and the sliders block the toggle controller in some configurations and expose the toggle controller in some configurations. In another preferred configuration, the handpiece includes two activation buttons, a toggle controller that has a toggle slider, and a slider that immobilizes the working arms and advances the blade while unlocking the toggle control slider. The handpiece may include two activation buttons, one toggle controller, and at least one slider, but preferably two sliders. The handpiece may include one or more and preferably a plurality of handpiece components.

The one or more handpiece components may be any device that is directly electrically connected, physically connected, carried on, or a combination thereof to the handpiece. The one or more handpiece components may be any component that may mechanically reconfigure the handpiece, be mechanically reconfigured by the handpiece, moved along the handpiece, apply a therapy current from the handpiece, or a combination thereof. The one or more handpiece components may be directly electrically connected to the handpiece so that power, signals, therapy currents, or a combination thereof flow directly to and/or from the handpiece or the handpiece component without travelling through an intervening device. The handpiece component may be located separate from the handpiece but electrically connected directly to the handpiece. For example a handpiece component may have a cord that is directly attached to the handpiece. Conversely, if the component connects to the handpiece through the generator the component is not a handpiece component. The one or more handpiece components and handpiece may be electrically reconfigurable so that the handpiece and the handpiece component are electrically connected in some configurations and electrically disconnected in some configurations. The one or more handpiece components may be a blade electrode, the first working arm, the second working arm, the ground pad, the slider, a monopolar electrode, one or more bipolar electrodes, or a combination thereof. Preferably, in one configuration the ground pad is placed discretely from the handpiece but the ground pad is directly electrically connected to the handpiece such that when the handpiece is in a monopolar configuration the ground pad is electrically activated. More preferably, the ground pad is not a handpiece component. The handpiece may provide power to the one or more handpiece components so that the handpiece components are not electrically connected directly to a power supply, a therapy current, a generator, or a combination thereof.

The present teachings are part of a system. The system as taught herein includes at least an electrosurgical device and a generator. The system may also include a remote electrode, power sources, or both. The generator may include one or more switches or preferably a plurality of switches internally that control the modes being supplied to the electrosurgical device. The generator may electrically control the therapy signals being provided to the electrosurgical device without physically moving switches. The generator switches may be one or more monopolar switches, one or more bipolar switches, one or more common switches, or a combination thereof. Preferably, the generator includes two or more bipolar switches, two or more monopolar switches, and one or more common switches for each mode (e.g., monopolar and bipolar). The generator may include one or more mode switches. The mode switches may convert the generator from a bipolar mode to a monopolar mode or vice versa. The mode switches may switch between bipolar and monopolar, cutting and coagulating, cutting and fulguration, or a combination thereof. The generator may be connected to one or more active portions that provide power to the electrosurgical device. Each active portion may provide power from the generator to the electrosurgical device for a specific mode. The generator may be connected to one or more return paths. The generator may include a return path for each of the modes so that each mode returns power through the return path to complete the circuit.

The present teachings may include one or more of the following features: wherein in the first configuration the first therapy signal passes between the first working arm and second working arm (and the blade does not electrically participate); wherein in the second configuration the device is configured to produce a plurality of therapy signals (different from the first electrosurgical therapy signal) at least one of which passes through the blade electrode; wherein the electrosurgical device includes a first slider, wherein the at least one slider in a second position: secures the first working arm and second working arm so that movement of the first working arm and the second working arm are prevented in a direction towards each other (i.e., lateral movement or rotational movement about its longitudinal axis), extends the blade electrode; wherein a first activation button and a second activation button, wherein in the first configuration the first activation button is configured to produce a first electrosurgical therapy signal, and in the second configuration the at least one of the one or more sliders disable the second activation button when the at least one slider is in a first slider position; wherein the at least one slider in a second position: (i) secures the first working arm and second working arm so that movement of the first working arm and the second working arm are prevented in a direction towards each other, (ii) extends the blade electrode, or (iii) enables the second activation button to produce a second electrosurgical therapy signal; and wherein a toggle control button is exposed when one or more sliders are in the second position, and the toggle controller is configured to: toggle the first activation button to produce either the first electrosurgical therapy signal, a third therapy signal, or both; or toggle the second activation button to produce either the second therapy signal or a fourth therapy signal, or both.

Figure 2:
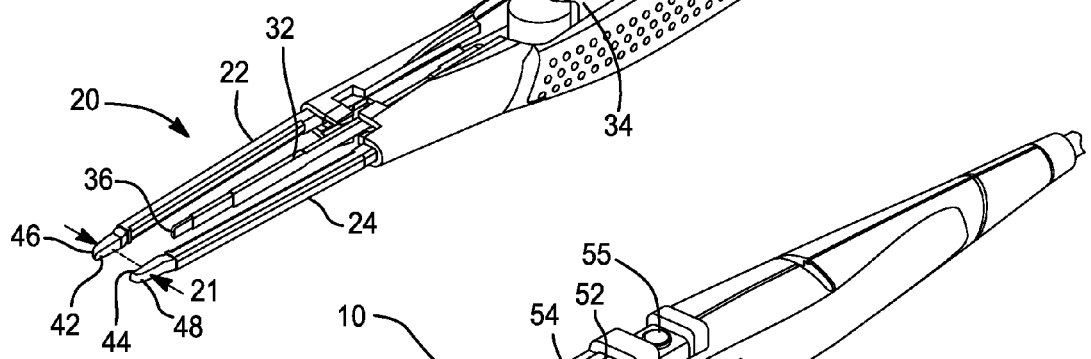
FIG. 2 is a perspective view of an electrosurgical device in a second configuration.
Figure 3:
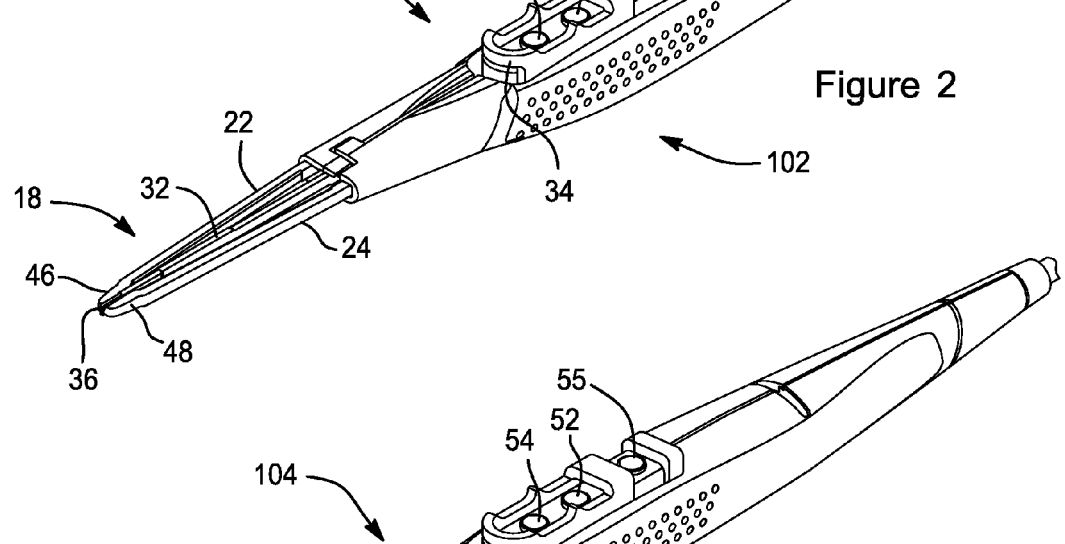
FIG. 3 is a perspective view of an electrosurgical device in a third configuration.

FIG. 1 depicts an electrosurgical device 10 comprising a forceps 20 with a central section 26 from which a first working arm (or jaw) 22 having a distal end 46, a second working arm (or jaw) 24 having a distal end 48, and an advanceable blade 32 with a blade electrode 30 extend. A cord 38 extends from the proximal end 28 of the central section 26 and connects the electrosurgical device 10 to an electrosurgical generator (not shown). The first working arm 22 and the second working arm 24 are biased apart from each other. The user can apply finger pressure on the first working arm 22 and the second working arm 24 to cause them to approach each other so as to grasp tissue (not shown). The first working arm 22 and second working arm 24 include a first electrode 42 and a second electrode 44. A first activation button 52 is located on the central section 26. When the user depresses the first activation button 52 the generator (not shown) can provide a first electrosurgical signal. For example, when the user depresses the first activation button 52 the generator produces a bipolar electrosurgical signal and delivers the bipolar electrosurgical signal to the first electrode 42 and the second electrode 44 to produce a bipolar current 62 that passes between the first electrode 42 and the second electrode 44. In the first configuration 100, the toggle control button 55 of the toggle controller and the second activation button 54 are blocked from use or hidden from view. The first slider blocks the second activation button 54 and the toggle control button 55 when in the first position. The characteristics of this electrosurgical current such as voltage, current, power, frequency, and duty cycle, may be configured specifically to coagulate tissue held between the first working arm 22 and second working arm 24. An advanceable blade electrode 30 is located between the first working arm 22 and the second working arm 24. The blade electrode 30 is shown in a first configuration 100 in which the blade electrode 30 is fully retracted to a proximal position. In the first configuration 100 the first working arm 22 and the second working arm 24 are free to move in a direction 21 towards each other. The blade 30 is connected to a first slider 34 that slides the blade 30 distally and proximally along the forceps 20 (see FIG. 2 for a distal position). When the first slider 34 is in its distal position the blade electrode 30 is advanced to an advanced position (FIGS. 2 and 3). When the first slider 34 is in a proximal position the blade electrode 30 is retracted to a retracted position (FIG. 1) where the distal end 36 of the blade 32 is located inside of the first working arm 22 and the second working arm 24. When the first slider 34 is in the proximal position the first working arm 22 with the first electrode 42 and the second working arm 24 with the second electrode 44 are movable toward each other in the direction 21 to grip tissue (not shown) therebetween FIG. 2 illustrates the blade 32, which includes a blade electrode 30 in a second position 102 which is a partially advanced position. The blade electrode 30 may be advanced so that its distal end 36 is flush, or substantially flush, with the distal ends 46, 48 of the first working arm 22 and the second working arm 24 so that a probe 18 is formed. Flush means for the blade to be extended so that the distal end 36 of the blade 32 is aligned with the distal ends 46, 48 of the first working arm 22 and the second working arm 24 or for the distal end 36 of the blade electrode 32 to be slightly retracted of or in line with the distal ends 46, 48 of the working arms 22, 24 (e.g., about 0.75 mm or less). A toggle control button 55 of the toggle controller is exposed by the slider 34 when the slider 34 in a forward position. When the slider 34 is in a distal position the exposed cut and coagulation buttons (52, 54) are configured to provide, for example, monopolar cut and monopolar coagulation and when the slider 34 is in a distal position the exposed cut and coagulation buttons 52, 54 may be configured to provide, for example, bipolar cut and bipolar coagulation.

FIG. 3 demonstrates the blade 32 and blade electrode 30 in the fully advanced position or third configuration 104 so that the distal end 36 and blade electrode 30 are advanced to extend beyond the distal ends 46, 48 of the first working arm 22 and second working arm 24. In the third configuration 104 the first activation button 52, second activation button 54, and the toggle control button 55 are all exposed.

Figure 4A:
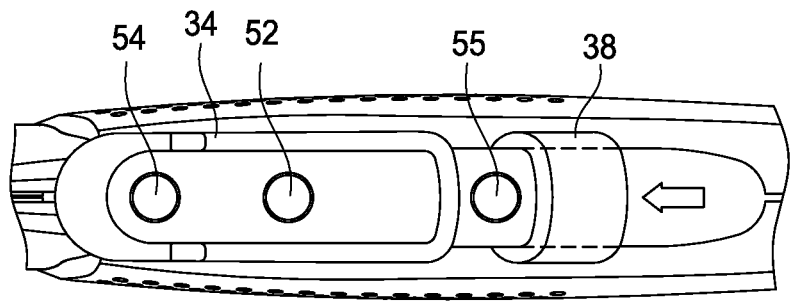
FIG. 4A is a close-up view of positioning of the buttons and sliders of the electrosurgical device.
Figure 4B:
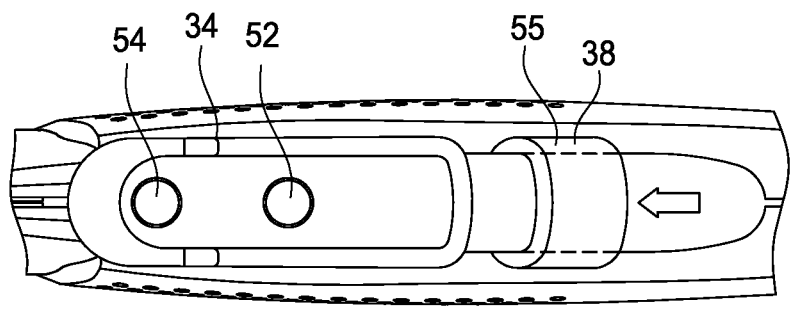
FIG. 4B is a close-up view of positioning of buttons and sliders of the electrosurgical device.
Figure 4C:
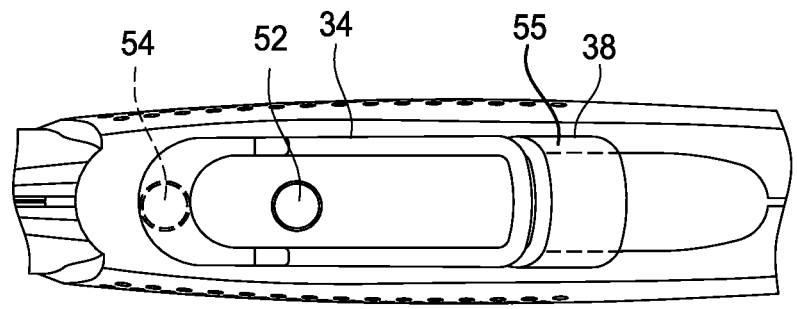
FIG. 4C illustrates a close-up view of a first slider in a first slider position that restricts movement of a second slider.

FIGS. 4A-4C are a close-up view of activation button configurations of the teachings herein. FIG. 4A illustrates a first activation button 52 and a second activation button 54 that are located proximate to a first slider 34. The first slider 34 as shown is not covering the second activation button 54 or the first activation button 52, but can be moved to cover one or both of the activation buttons. The second slider 38 is moved in the direction of the arrow to expose the toggle control button 55 so that the modes of the electrosurgical device can be changed.

FIG. 4B illustrates the first activation button 52 and a second activation button 54 that are located proximate to a first slider 34. The first slider 34 as shown is not covering the second activation button 54 or the first activation button 52, but can be moved to cover one or both of the activation buttons. The second slider 38 is a toggle control button 55 that can be moved between two or more positions to toggle between modes so that the first activation button 52 and the second activation button 54 provide different therapy currents. As shown, the first slider 34 is advanced forward so that the second slider 38 is permitted to move from the first position.

FIG. 4C illustrates the second activation button 54 covered by the first slider 34 in a first slider first position. The second activation button 52 is accessible through the first slider 34 so that the first activation button is accessible. The first slider 34 abuts the second slider 38 and prevents the second slider 38 from moving from the second slider first position to the second slider second position. The second slider 38 is a toggle control button 55 that changes modes of the electrosurgical device when the toggle control button 55 is moved between positions.

Figure 5A:
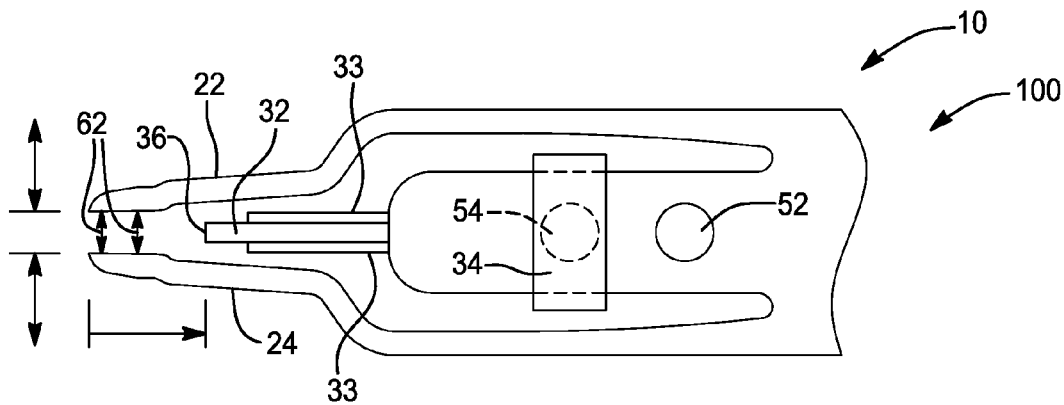
FIG. 5A illustrates positioning of the components in the first configuration.
Figure 5B:
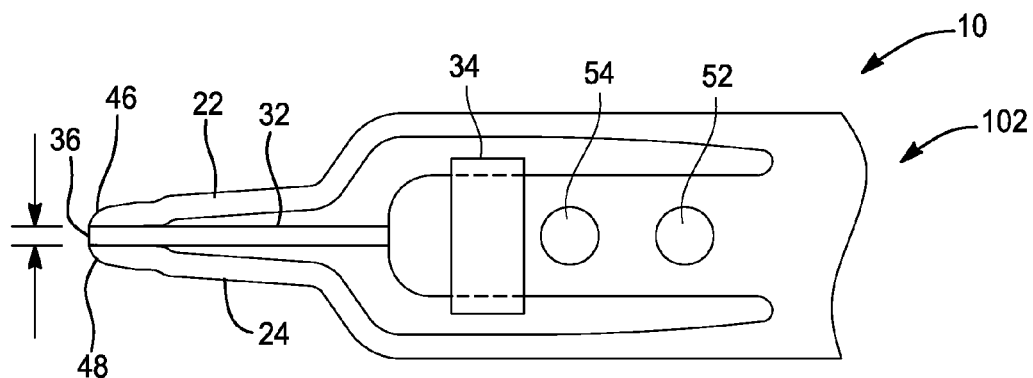
FIG. 5B illustrates positioning of the components in the second configuration.
Figure 5C:
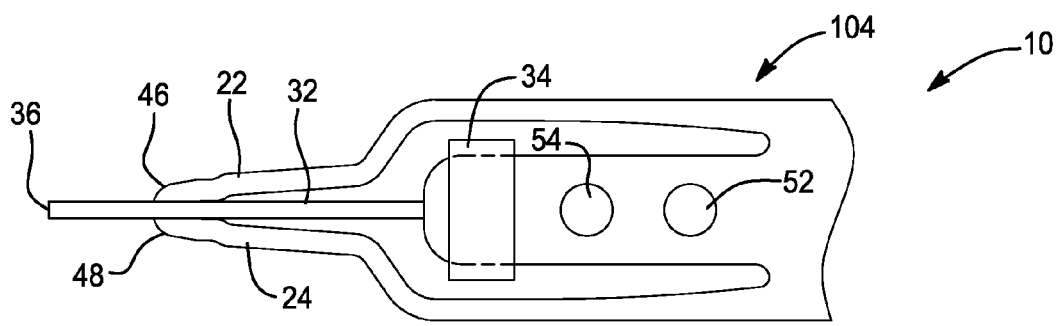
FIG. 5C illustrates positioning of the components in the third configuration.

FIGS. 5A-5C illustrate the electrosurgical device 10 switching between the first configuration 100, second configuration 102, and third configuration 104. FIG. 5A illustrates a first configuration 100 of the electrosurgical device 10 where the blade 32 is in a retracted state so that a distal end 36 of the blade 32 is located within a region between the first working arm 22 and the second working arm 24 so that bipolar current 62 can pass between the first working arm 22 and the second working arm 24. The first working arm 22 and the second working arm 24 are located a distance apart so that an anatomical feature such as tissue (not shown) may be gripped therebetween. The distal end 36 of the blade 32 is retracted a sufficient distance that the distal end 36 does not interfere with the gripping of the anatomical feature (not shown). As shown, in the first configuration 100, the second activation button 54 is covered by a first slider 34 and the first activation button 52 is exposed so that upon depression of the first activation button 52 the bipolar current 62 is passed between the first working arm 22 and the second working arm 24. The blade 32 includes insulation 33 to prevent a transfer of current from an unintended location of the blade 32 although the blade may be free of insulation as shown in FIGS. 5B-5C. The insulation 33 when present prevents from the flow of power from the blade to the working arms or vice versa. The insulation may be located on the working arms (not shown).

FIG. 5B illustrates the second configuration 102 of the electrosurgical device 10 where the distal end 36 of the blade 32 is flush with the distal end 46 of the first working arm 22 and the distal end 48 of the second working arm 48. The first working arm 22 and second working arm 24 prevent movement of the blade 32 by gripping the blade in the flush position. The first slider 34 is moved into an intermediate position so that both the first activation button 52 and second activation button 54 are exposed and the blade is moved to a substantially flush position.

FIG. 5C illustrates the third configuration 104 wherein the distal end 36 of the blade 32 extends between the distal end 46 of the first working arm 22 and the distal end 48 of the second working arm 24. The first slider 34 is moved into a distal position where both the first activation button 52 and the second activation button 54 are exposed so that two different currents can be applied through the electrosurgical device 10.

Figure 6A:
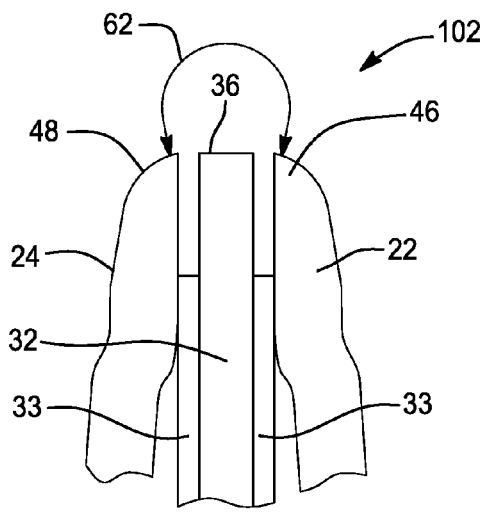
FIG. 6A illustrates the electrosurgical device in a second configuration with a bipolar current.

FIGS. 6A-6D illustrate a close up view of the tip of an electrosurgical device 10 in different electrosurgical configurations. FIG. 6A shows the tip in the second configuration 102 with the distal end 36 the blade 32 flush with the distal end 46 of the first working arm 22 and the distal end 48 of the second working arm 24. The first working arm 22 and the second working arm 24 are spaced apart by the blade 32 and insulation 33 and in contact the insulation 33 on opposing sides of the blade 32. A bipolar current 62 is shown passing between the first electrode 42 of the first working arm 22 and the second electrode 44 of the second working arm 24 and around the distal end 36 of the blade 32.

Figure 6B:
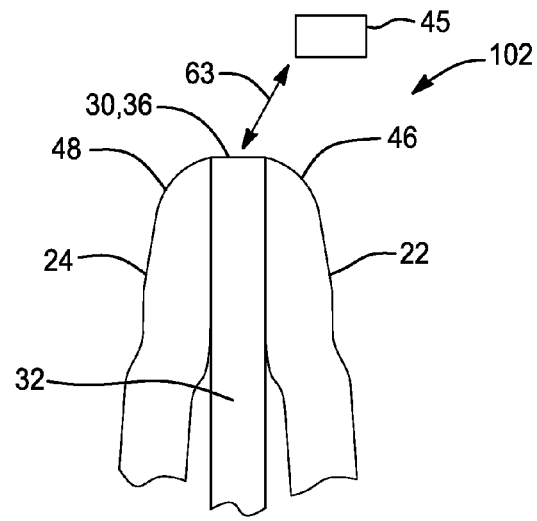
FIG. 6B illustrates the electrosurgical device in a second configuration with a monopolar coagulation current.

FIG. 6B shows a second configuration 102 with monopolar current 63 extending from the blade electrode 30 of the blade 32 to a remote electrode 45 through tissue (not shown). This current may be specifically configured for coagulating tissue (not shown) by monopolar current 63 extending from the distal end 36 to the remote electrode 45. The distal end 36 of the blade 32 is flush with the distal end 46 of the first working arm 22 and the distal end 48 of the second working arm 24.

Figure 6C:
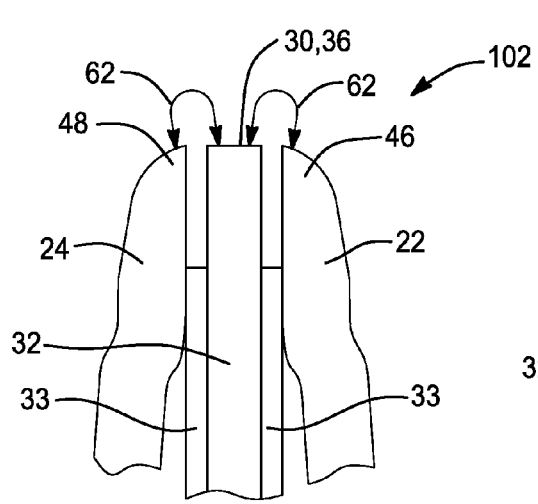
FIG. 6C illustrates the electrosurgical device in a second configuration with a bipolar coagulation current.

FIG. 6C shows a second configuration 102 with a bipolar current 62 extending from the blade electrode 30 of the blade 32 to one or both of the first electrode 42 or second electrode 44 in the respective first working arm or second working arm 22, 24 when the toggle control button 55 (not shown) is toggled to a different position than that of FIG. 4A. The bipolar current 62 may be specifically configured for cutting tissue when, for example the second activation button (54) (not shown) is pressed and the toggle control button (55) (not shown) is in a bipolar state. As shown, the distal end 36 of the blade 32 and the distal ends 46, 48 of the first working arm 22 and second working arm 24 are flush and the bipolar current 62 flows from the blade 32 to the first working arm 22, the second working arm 24, or both. The distal end 46 of the first working arm 22 and the distal end 48 of the second working arm 24 are spaced apart from by the blade 32 and insulation 33 so that the blade 32 and working arms 22, 24 are electrically isolated and the current flows through the anatomical features such as tissue (not shown).

Figure 6D:
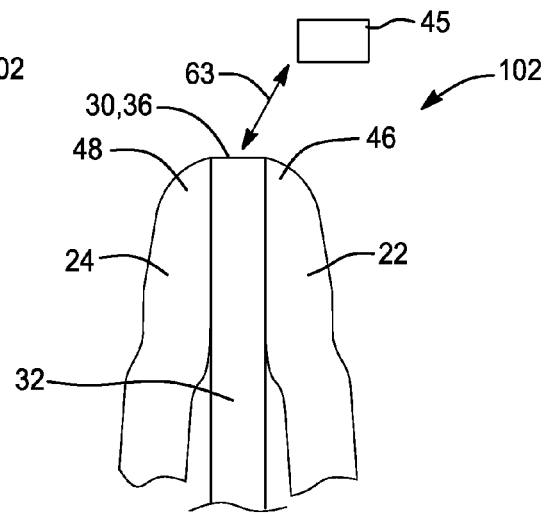
FIG. 6D illustrates the electrosurgical device in a second configuration with a monopolar cut current.

FIG. 6D shows a second configuration 102 with monopolar current 63 passing from the blade electrode 30 in the distal end 36 of the blade 32 through tissue (not shown) and to a remote electrode 45. This monopolar current 63 is specifically configured for cutting tissue (not shown) when, for example the second activation button cut button (not shown) is pressed and the toggle control button (not shown) is in a monopolar state. The distal end 36 of the blade 32 is flush with the distal end 46 of the first working arm 22 and the distal end 48 of the second working arm 24. Although not shown, the blade 32, working arms, or both may include insulation.

Figure 7A:
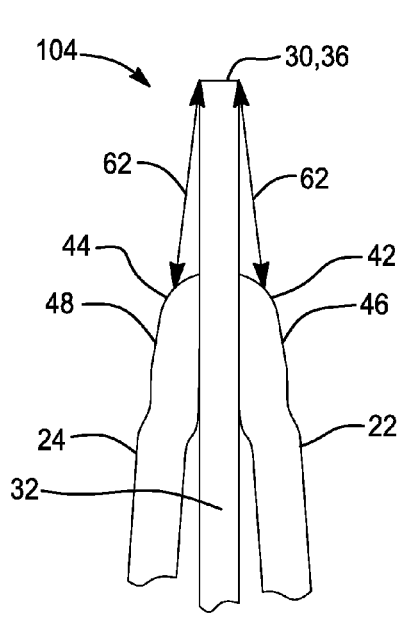
FIG. 7A illustrates the electrosurgical device in a third configuration with a bipolar current.

FIG. 7A is a third configuration 104 with bipolar current 62 passing between the blade electrode 30 at the distal end 36 of the blade 32 and the first electrode 42 at the distal end 46 of the first working arm 22 and the second electrode 44 at the distal end 48 of the second working arm 24. The distal end 36 of the blade 32 extends beyond the distal end 46 of the first working arm 22 and the distal end 48 of the second working arm 24. The first working arm 22 and the second working arm 24 are in contact with the blade 32.

Figure 7B:
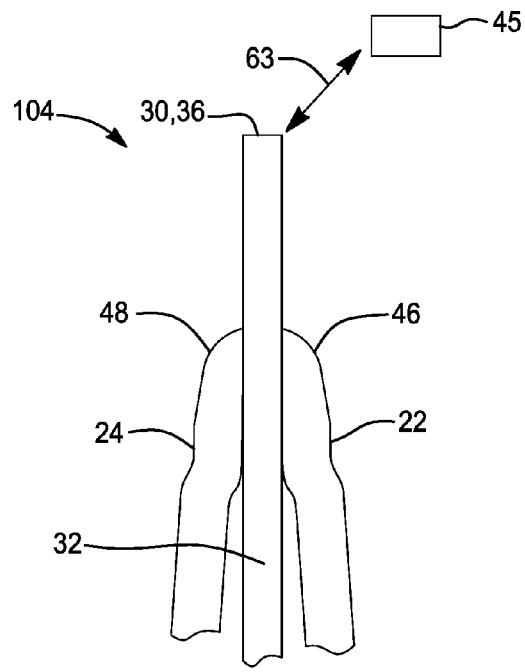
FIG. 7B illustrates the electrosurgical device in a third configuration with a monopolar current.

FIG. 7B is a third configuration 104 with monopolar current 63 passing from a blade electrode 30 located at a distal end 36 of the blade 32 to a remote electrode 45. The distal end 36 of the blade 32 is extended beyond a distal end 46 of the first working arm 22 and a distal end 48 of the second working arm 24. The first working arm 22 and the second working arm 24 are in contact with the blade 32.

Figure 8:
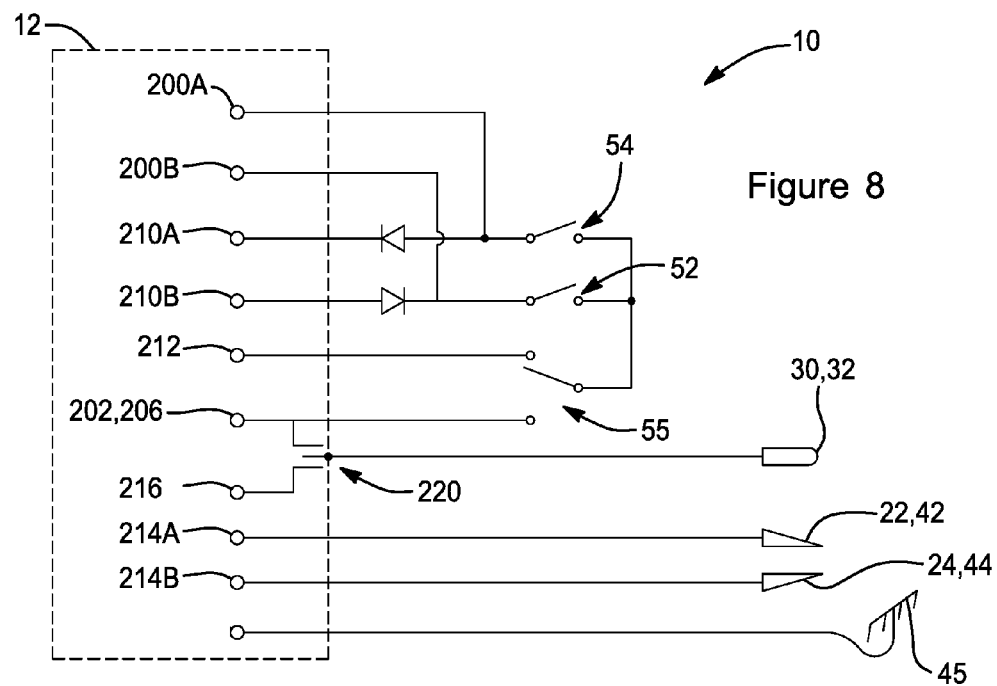
FIG. 8 an electrical circuit of the electrosurgical device taught herein.

FIG. 8 is a schematic view of electrical connections between an electrosurgical device 10 and a generator 12. The generator includes a monopolar switch return 202 and a bipolar switch return 212. The generator 12 includes a first monopolar switch lead 200A and a first bipolar switch lead 210A that are connected to the second activation button 54 and through the toggle button 55 to one of the monopolar switch return 202 and a bipolar switch return 212; thereas to switch the second activation button 54 between a first monopolar state and a first bipolar state. The generator 12 includes a second monopolar switch lead 200*b* and a second bipolar switch lead 210*b* that are connected to the first activation button 52 and through the toggle button 55 to one of the monopolar switch return 202 and a bipolar switch return 212; thereas to switch the first activation button 52 between a second monopolar state and a second bipolar state. During use a toggle control button 55 switches the electrosurgical device 10 between a monopolar common switch 202 and a bipolar common switch 212 so that monopolar energy or bipolar energy are applied depending on whether the toggle control button 55 is toggled to the monopolar switch 202 or the bipolar switch 212. Switching the toggle control button 55 switches the first activation button 52 between a monopolar switch 200B and a bipolar switch 210B and a second activation button 54 between a monopolar switch 200A and a bipolar switch 210A so that a user can actively select to apply a monopolar current or a bipolar current. The blade electrode 32 in the blade 30 can be switched between a monopolar active 206 and a bipolar active 216 by changing a monopolar switch/bipolar switch 220. The first electrode 42 located within the first working arm 22 is connected to a bipolar return 214A and the second electrode 44 located within the second working arm 24 is connected to a bipolar return 214B so that current can extend between the first working arm 22 and the second working arm 24 or from the blade electrode 32 and the first working arm 22 and/or the second working arm 24. A remote electrode 45 is located a distance away from the electrosurgical device 10 and bipolar current flows from the blade electrode 32 to the remote electrode 45.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:
1. An electrosurgical device comprising:
   a. forceps including:
      a first working arm, and
      a second working arm;
   b. a blade;
   c. one or more sliders that move along the forceps between at least a first position and a second position;
   d. a first activation button; and
   e. a second activation button;
   wherein the electrosurgical device is capable of being switched between:
   A. a first configuration wherein:
      the first working arm and the second working arm are free to move in a direction towards each other so as to grasp tissue therebetween,
      the blade is retracted within a distal end of the first working arm and a distal end of the second working arm, and
      the first activation button is configured to produce a first therapy signal; and
   B. a second configuration wherein:
      the first working arm and the second working arm are secured together to prevent movement in a direction towards each other, and
      the blade is extended so that a distal end of the blade is substantially flush with the distal end of the first working arm and the distal end of the second working arm;
   wherein at least one of the one or more sliders disable the second activation button when the at least one slider is in the first position, and
   wherein the at least one slider in the second position: secures the first working arm and the second working arm so that movement of the first working arm and the second working arm are prevented in a direction towards each other, extends the blade, or enables the second activation button to produce a second therapy signal.

2. The electrosurgical device of claim 1 wherein,
   a toggle control button of a toggle controller is exposed when one or more sliders are in the second position; and
      the toggle controller is configured to:
         toggle the first activation button to produce either the first therapy signal, a third therapy signal, or both; or
         toggle the second activation button to produce either the second therapy signal or a fourth therapy signal, or both.

3. The electrosurgical device of claim 2, wherein the first therapy signal is bipolar coagulation.

4. The electrosurgical device of claim 2, wherein the second therapy signal is bipolar cut and the fourth therapy signal is monopolar cut.

5. The electrosurgical device of claim 2, wherein the second therapy signal or the fourth therapy signal is monopolar cut or bipolar cut.

6. The electrosurgical device of claim 2, wherein the one or more sliders disable the toggle controller when the one or more sliders are in the first position.

7. The electrosurgical device of claim 1, wherein the electrosurgical device includes a third configuration where the blade is extended beyond the distal end of the first working arm and the second working arm.

8. The electrosurgical device of claim 7, wherein a toggle control button of a toggle controller is exposed when the electrosurgical device is in the third configuration so that the toggle controller is configured to:
 toggle the first activation button to produce either the first therapy signal, a third therapy signal, or both; or
 toggle the second activation button to produce either the second therapy signal or a fourth therapy signal, or both.

9. The electrosurgical device of claim 1, wherein the one or more sliders are a first slider and a second slider.

10. The electrosurgical device of claim 9, wherein the first slider covers the first activation button, the second activation button, or both in one or more positions.

11. The electrosurgical device of claim 9, wherein the second slider is prevented from moving when the first slider is in the first position and permitted to move when the first slider is in the second position.

12. The electrosurgical device of claim 9, wherein the first slider, the second slider, or both are movable from the first position, to the second position, and a third position.

13. The electrosurgical device of claim 12, wherein the first slider when in the third position extends the distal end of the blade beyond the distal end of the first working arm and the distal end of the second working arm.

14. The electrosurgical device of claim 9, wherein a blade is movable with the first slider or the second slider.

15. The electrosurgical device of claim 9, wherein the first slider when in the first position positions the distal end of the blade within the distal end of the first working arm and the distal end of the second working arm.

16. The electrosurgical device of claim 9, wherein the first slider when in the second position aligns the distal end of the blade with the distal end of the first working arm and the distal end of the second working arm so that the distal end of the blade and the distal end of the first working arm and the distal end of the second working arm are flush.

17. An electrosurgical device comprising:
 forceps including:
  (i) a first working arm,
  (ii) a second working arm,
  (iii) a first activation button,
  (iv) an optional second activation button,
  (v) one or more sliders, and
  (vi) a toggle controller;
 wherein the electrosurgical device is capable of being switched between:
 a first configuration wherein:
  a toggle control button of the toggle controller is inactive or blocked when the slider is in a first position, and
  a first therapy signal passes between the first working arm and the second working arm; and;
 a second configuration wherein:
  the toggle control button is exposed when one of the one or more sliders are in a second position; and
  the toggle controller is configured to:
   toggle the first activation button to produce either the first therapy signal, a signal therapy signal, or both.

18. The electrosurgical device of claim 17, wherein the one or more sliders include a second slider that covers the toggle control button of the toggle controller in one or more positions so that the toggle control button is not accessible in at least one position.

19. The electrosurgical device of claim 17, wherein the electrosurgical device includes the second activation button and the one or more sliders include a second slider that is the toggle control button and the toggle control button switches between a bipolar state and a monopolar state where the first activation button, the second activation button, or both produce a monopolar signal in the monopolar state and a bipolar signal in the bipolar state.

20. The electrosurgical device of claim 19, wherein the second slider has an off state where the toggle control button is deactivated.

21. An electrosurgical device comprising:
 a. a first working arm and a second working arm
 b. a first slider that moves between at least a first slider first position and a first slider second position;
 c. a second slider that moves between at least a second slider first position and a second slider second position;
 d. a first activation button; and
 e. a second activation button;
 wherein when the first slider is in the first slider first position:
  (i) the first working arm and the second working arm are free to move in a direction towards each other so as to grasp tissue therebetween,
  (ii) the first activation button is configured to produce a first therapy signal,
  (iii) the second activation button is blocked or disabled, and
  (iv) the second slider is prevented from moving from the second slider first position by the first slider, and
 wherein when the first slider is in the first slider second position:
  (i) the second activation button is configured to produce a second therapy signal, and
  (ii) the second slider is permitted to move between the second slider first position and the second slider second position.

22. The electrosurgical device of claim 21, wherein the electrosurgical device comprises
 a forceps including:
  the first working arm, and
  the second working arm;
 wherein when the first slider is in the first slider first position the first working arm and the second working arm are free to move in a direction towards each other so as to grasp tissue therebetween; and
 wherein when the second slider is in the second slider second position the first working arm and the second working arm are immobilized from movement in the direction towards each other.

23. The electrosurgical device of claim 22, wherein when the second slider is in the second slider first position the first working arm and the second working arm are free to move in the direction towards each other so as to grasp tissue therebetween.

24. The electrosurgical device of claim 21, wherein the electrosurgical device includes
- a forceps including:
  - the first working arm,
  - the second working arm; and
  - a blade,
- wherein when the first slider is in the first slider first position a distal end of the blade is at a first blade position, and
- wherein when the second slider is in the second slider second position the distal end of the blade is at a second blade position that is different from the first blade position.

25. The electrosurgical device of claim 24, wherein when the second slider in the second slider first position, the distal end of the blade is in the first blade position.

26. The electrosurgical device of claim 24, wherein the blade, in the first blade position, is retracted so that a distal end of the blade is located proximal of the first working arm and the second working arm, and
- wherein the blade, in the second blade position, is extended to be substantially flush with or extend beyond a distal end of the first working arm and a distal end of the second working arm.

* * * * *

UNITED STATES PATENT AND TRADEMARK OFFICE
CERTIFICATE OF CORRECTION

Page 1 of 1

PATENT NO. : 9,707,028 B2
APPLICATION NO. : 14/830255
DATED : July 18, 2017
INVENTOR(S) : Batchelor et al.

It is certified that error appears in the above-identified patent and that said Letters Patent is hereby corrected as shown below:

In the Claims

Column 24 Line 8, Claim 17 delete "a signal therapy signal" and insert --a second therapy signal--

Signed and Sealed this
Fifth Day of September, 2017

Joseph Matal
*Performing the Functions and Duties of the*
*Under Secretary of Commerce for Intellectual Property and*
*Director of the United States Patent and Trademark Office*